United States Patent [19]

Mutzel et al.

[11] 4,367,216
[45] Jan. 4, 1983

[54] TRIIODINATED 5-AMINOISOPHTHALIC ACID DERIVATIVES

[75] Inventors: Wolfgang Mutzel; Hans-Martin Siefert; Ulrich Speck; Heinrich Pfeiffer; Paul-Eberhard Schulze; Bernhard Acksteiner, all of Berlin, Fed. Rep. of Germany

[73] Assignee: Schering Aktiengesellschaft, Berlin and Bergkamen, Fed. Rep. of Germany

[21] Appl. No.: 163,895

[22] Filed: Jun. 27, 1980

[30] Foreign Application Priority Data

Jun. 28, 1979 [DE] Fed. Rep. of Germany ....... 2926428
Oct. 26, 1979 [DE] Fed. Rep. of Germany ....... 2943777
May 2, 1980 [DE] Fed. Rep. of Germany ....... 3017304

[51] Int. Cl.$^3$ ............................................. A61K 49/04
[52] U.S. Cl. ........................................ 424/5; 260/550;
564/153; 556/419; 556/434
[58] Field of Search ........................... 564/153; 424/5;
260/550; 556/419, 434

[56] References Cited

U.S. PATENT DOCUMENTS 4,139,605 2/1979 Felder et al. .......................... 424/5
4,239,747 12/1980 Pfeiffer et al. ....................... 564/153

OTHER PUBLICATIONS

Siefert et al, Lymphology 13 (1980), 150-157.

Miklautz et al, Preprint.

*Primary Examiner*—Delbert R. Phillips
*Attorney, Agent, or Firm*—Millen & White

[57] ABSTRACT

Compounds of the formula

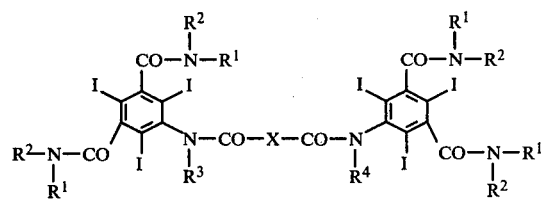

wherein
$R^1$ is hydroxy-$C_{2-8}$-alkyl containing 1-5 OH-groups;
$R^2$ is hydrogen, $C_{1-4}$-alkyl or $R^1$;
$R^3$ and $R^4$ can be identical or different, and each independently is hydrogen or $C_{1-4}$-alkyl; and
X is straight chain or branched $C_{2-12}$ alkylene interrupted by sulfur or selenium atoms, and, optionally, additionally interrupted by oxygen atoms, by a di($C_{1-4}$-alkyl)silyl group or a tetra($C_{1-4}$-alkyl)-disiloxane group;
are very useful as X-ray contrast media opaque agents, which can be employed even in lymphography.

15 Claims, No Drawings

TRIIODINATED 5-AMINOISOPHTHALIC ACID DERIVATIVES

BACKGROUND OF THE INVENTION

The present invention relates to novel tri-iodinated 5-aminoisophthalic acid derivatives.

In the field of X-ray diagnostics, for example, for visualization of the urine-excreting organs and the vessels to be detected angiographically, well compatible salts of 2,4,6-triiodobenzoic acids have been developed as the contrast media. These substances, however, are not tolerated by the host organisms without side effects at higher dosages, although their toxicity is frequently low. Adequate representation of the vascular system, the urinary tract, and also the cerebrospinal cavities and other systems, requires the use of high dosages of contrast medium or of highly concentrated solutions. Thus, the physicochemical properties of the contrast media and their solutions are of particular importance since essential pharmacological effects, such as pain, drop in blood pressure, vascular damage, and many others are attributed to these properties.

With the development of dimers of such compounds, obtained by linking together two triiodinated benzoic benzoic acids, it has been possible, inter alia, to improve neural compatibility and reduce vasodilation in angiography as compared to the monomeric triiodinated benzoic acids. Due to the somewhat lower osmotic pressure associated with such dimers, for example, of the dimeric iocarmic acid (as the dimeglumine salt), the concentration in the urine is increased.

With the introduction of the nonionic metrizamide, it has been possible for the first time to significantly lower the osmotic pressure in a monomeric, triiodinated contrast medium. Also in metrizamide, the osmotic pressure of a solution, suitable for example for angiography (300 mg iodine/ml) is, at 12 atmospheres, still considerably above the osmotic pressure of the blood (7.5 atmospheres). Its suitability for myoelography, angiography and urography has been described in several articles in Acta Radiol. Suppl. 335 (1973).

However, all heretofore described water-soluble contrast media, just as metrizamide, are useless for lymphography in which the physical properties of the X-ray contrast medium also play an important role. In medical practice, iodinated oils, e.g., iodinated fatty acid esters of poppy oil are presently used predominantly for lymphography. These agents, on the one hand, show a good storage capability in the lymph nodes and a good contrast effect, but, on the other hand, cannot be used generally nor without problems due to their known side effects. In view of the fact that lymphatic vessels can be injured readily, especially in the case of too rapid an administration, these media can promote lesions of the lymphatic vessels. A number of disadvantages are due to the oily character of these contrast media: since suspension of the oil takes place only in the blood, the size of the oil droplets cannot be predetermined. If the oil droplets are too large, oil microembolisms, for example, in the lungs, are frequently unavoidable. Since the absorption of the large oil droplets into the interstitial cavities in the lymphatic capillaries is hardly possible, a visualization of the lymphatic channels and lymph nodes, for example, after subcutaneous or intraparenchymatous injection, is accomplished only in rare cases.

The latter disadvantage can only be overcome by endolymphatic application, but in this case it is necessary to first mark the medium with a dye, which likewise is not without complications, and an operative uncovering of the lymphatic vessels under local anesthesia must be carried out. Finally, the contrast media based on these iodinated oils are excreted only very gradually after application. Depending on the form of preparation, the excretion period can be weeks to months.

Attempts have been made to overcome the above-described disadvantages by an emulsification of these iodinated oils. Although the viscosity and the droplet size have thus been reduced, whereby the capillary passage could be improved and, if the emulsion was stable, the risk of embolism formation could be lowered, such partial success has been at the cost of incurring other disadvantages. Examples which may be mentioned in this connection are: an effective reduction of the iodine content per milliliter of contrast medium and a concomitant, unavoidable loss in contrast; a higher local toxicity on lymph nodes; hepatotoxic effects; and a histologically detectable foreign-body reaction, aggravated by the added emulsifiers.

All contrast media based on iodinated oils possess low stability and can be used only to a limited extent because of the above-described side effects.

The conventional, water-soluble, organic iodine compounds used in the conventional preparations for uro- and angiography have also proved to have little or no suitability for lymphography, because they diffuse too quickly out of the lymphatic vessel system after application. Due to this lack of storage capability in the lymph nodes, these aqueous forms of preparations are suitable, within limits at best, for peripheral lymphangiography.

Also, experiments with crystalline suspensions based on nuclear-iodinated aromatics, such as, for example, iodamide or tetraiodoterephthalic acid derivatives, have failed to produce contrast media for lymphography useful in medical practice. Such media possess insufficient compatibility (inflammation manifestations at the injection site and in the lymphatic system) and excessively long excretion periods (days to weeks).

In summation, it can be seen that lymphograhy with these conventional X-ray contrast media is impossible without involving risk. It, thus, can be conducted only on an in-patient basis. Further, the patient must be tested very carefully for his/her suitability for this examination. At least three days are required for conducting such an examination, including the suitability test and the actual lymphography.

SUMMARY OF THE INVENTION

Accordingly, it is an object of the present invention to provide novel opaquing compounds based on nuclear-iodinated aromatics and X-ray contrast media containing them, which are applicable for the visualization of body cavities in general and also for lymphography in particular, and which avoid the foregoing disadvantages.

Upon further study of the specification and appended claims, further objects and advantages of this invention will become apparent to those skilled in the art.

These objects have been attained, in one aspect of this invention, by providing compounds of Formula I

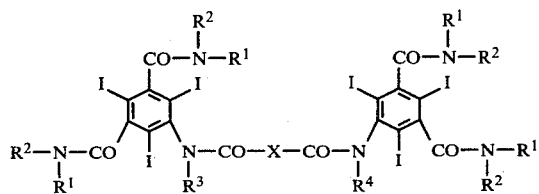

wherein

R[1] is lower, straight-chain or branched, mono- or polyhydroxyalkyl,

R[2] is hydrogen, lower alkyl or R[1],

R[3] and R[4], which can be identical or different, independently are each hydrogen or lower alkyl, and X is a straight-chain or branched alkylene interrupted by one or more sulfur or selenium atoms and, optionally, additionally interrupted by oxygen atoms, di(lower alkyl)silyl or a tetra(lower alkyl)disiloxane group.

The invention also related to a process for the preparation of the compounds of Formula I, to radiopaque media containing them as the opaque agent, and to intermediates of Formula II recited below, which are used to prepare the compounds of Formula I.

DETAILED DISCUSSION

R[1] as the straight-chain or branched, lower, mono- or polyhydroxyalkyl residue, may contain 2–8 carbon atoms, preferably 2–5 carbon atoms. Straight-chain residues R[1] preferably are of 2–4 carbon atoms; branched-chain residues preferably are of 3–5, especially 3 carbon atoms. The hydroxy groups in R[1] can be primary or secondary ones. The residue R[1] can contain 1–5 hydroxy groups; 1–3, and, especially, 2 hydroxy groups are preferred. Examples of R[1] include: 2-hydroxyethyl, 2-hydroxypropyl, 3-hydroxypropyl, 3-hydroxy-1-methylpropyl, 1-(hydroxymethyl)ethyl, 3-hydroxy-1-methylbutyl, 2-hydroxyisobutyl, 2,3-dihyroxypropyl, 2,3-dihydroxybutyl, 2,4-dihydroxybutyl, 3,4-dihydroxybutyl, 3-hydroxy-2-(hydroxymethyl)propyl, 2-hydroxy-3-(hydroxymethyl)propyl, 2,3-dihydroxy-1-methylpropyl, 2-hydroxy-3-(hydroxymethyl)butyl, 1,3,4-trihydroxybutyl, 2,3,4-trihydroxybutyl, 2,4-dihydroxy-3-(hydroxymethyl)butyl, 3-hydroxy-2-bis(-hydroxymethyl)propyl, 4-hydroxy-3,3-bis(hydroxymethyl)butyl, 4-hydroxy-2,2-bis(hydroxymethyl)butyl, 2-hydroxy-1,1-bis(hydroxymethyl)ethyl, —CH$_2$—(CH.OH)$_4$.CH$_2$.OH, etc.

The lower alkyl residues as R[2], R[3] and R[4] include especially straight-chain residues of 1–4 carbon atoms, preferably 1–2 carbon atoms, such as, for example, butyl, propyl, ethyl, and especially methyl. However, branched C$_{3-4}$ alkyl groups are also possible.

X can be of 2–12, preferably 2–8, carbon atoms within its definition as a straight-chain or branched alkylene interrupted by one or moe (e.g., 1–4) sulfur or selenium atoms, or mixtures thereof, and optionally additionally interrupted by oxygen atoms (e.g., 1–3), by a di(lower alkyl)-silyl group or by a tetra(lower alkyl)disiloxane group. Particularly suitable as X is a straight-chain alkylene of 2–4 carbon atoms which is interrupted by one or more of S or Se, preferably by one, two or three sulfur or one or two selenium atoms, or by a di(lower alkyl)silyl group or a tetra(lower alkyl)disiloxane group, lower referring in general to 1–4 carbon atoms. Suitable lower alkyl substituents in these Si-containing groups include, in particular, straight-chain alkyl of 1–4, preferably 1–2 carbon atoms; examples include butyl, propyl, ethyl, and, especially, methyl. A suitable structure can also be a straight-chain alkylene of 2–4 carbon atoms interrupted by —S—S—, —Se—Se—, —S—Se—.

If X is a branched alkylene, the thus-contained alkyl substituent on the main chain is preferably a lower alkyl residue of 1–4 carbon atoms, especially, methyl or also ethyl.

Examples of X include: —CH$_2$.CH$_2$.S.CH$_2$.CH$_2$—, —CH$_2$—S—S—CH$_2$—, —CH$_2$.CH$_2$—S—S—CH$_2$.CH$_2$—, —CH$_2$—S—CH$_2$ CH$_2$—S—CH$_2$—, —CH$_2$.S—CH$_2$.CH$_2$ CH$_2$.CH$_2$.S.CH$_2$—, —CH$_2$—S—CH$_2$—S—CH$_2$, —CH$_2$.CH$_2$—S—CH$_2$—S—CH$_2$.CH$_2$—,

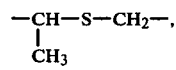

—CH$_2$.CH$_2$—Se—CH$_2$.CH$_2$—, —CH$_2$.S.CH$_2$.CH$_2$—, —CH$_2$—S—CH$_2$.CH$_2$.CH$_2$—, —CH$_2$.CH$_2$—S—CH$_2$—CH$_2$—CH$_2$—, —CH$_2$—O—CH$_2$—CH$_2$—S—CH$_2$—,

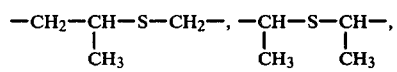

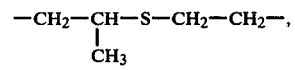

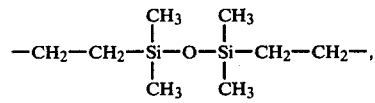

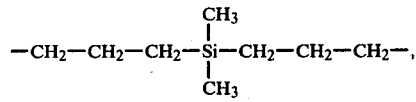

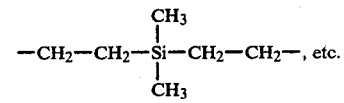

The present invention also relates to a process for preparing triiodinated 5-aminoisophthalic acid derivatives of Formula I, comprising, reacting in a conventional manner, a tetracarboxylic acid tetrachloride of Formula II

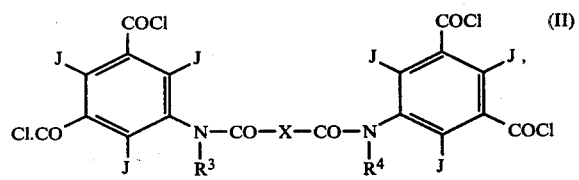

wherein R[3], R[4] and X are as defined above, with an amine

wherein $R^1$ and $R^2$ are as defined above.

The amidation of the CO.Cl groups is conducted in a suitable, advantageously polar, solvent at 0°–100° C., preferably at 20°–80° C. Examples of suitable solvents include dioxane, tetrahydrofuran, dimethylformamide, dimethylacetamide, hempa, and similar compounds, and mixtures thereof. Since the amidation reaction takes place exothermally, it may be advantageous to slightly cool the reaction mixture to be able to keep the reaction temperature at below 60° C.

The hydrogen chloride liberated during the amidation reaction is bound either by a corresponding excess of base

or by adding a customary proton acceptor. Advantageously, tertiary amines, such as, for example, triethylamine or tributylamine, are utilized as such proton acceptors to neutralize the hydrogen chloride produced during the amidation.

The inorganic or organic salts obtained during the course of the reaction are conventionally separated, advantageously, for example, with the aid of customary ion-exchange columns or by filtration over known adsorbents, e.g., "Diaion" or "Amberite" XAD-2 and 4.

The novel tetracarboxylic acid tetrachlorides of Formula II used in the process are obtained by methods known per se from the conventional 5-amino- or 5-lower-alkyl-amino-2,4,6-triiodoisophthalic acid dichloride by condensation with the dichloride of an aliphatic dicarboxylic acid of the formula Cl—CO—X—CO—Cl wherein X is as defined above. The reaction takes place preferably at above 100° C. Suitable reaction media include organic solvents, e.g., aromatic hydrocarbons, such as chlorobenzene and toluene, but especially inert polar solvents, such as dimethylacetamide, N-methylpyrrolidone, dioxane, tetrahydrofuran, and others. The dimeric tetracarboxylic acid tetrachlorides of Formula II formed during the reaction are either crystallized or are isolated by concentrating the solution under vacuum.

If the substituents $R^3$ and $R^4$ are different in the tetracarboxylic acid tetrachloride of Formula II (e.g., $R^3$=H, $R^4$=lower alkyl, preferably methyl), then the reaction is conducted stepwise by conventionally reacting, for example as described above, a 5-lower-alkylamino-2,4,6-triiodoisophthalic acid dichloride with Cl.CO—X—COOCH$_3$ (X being as defined above), conventionally saponifying the thus-formed monoester, and isolating the trioic acid in the form of its sodium salt. The Na salt is subsequently conventionally converted into the corresponding tricarboxylic acid trichloride, for example, with phosphorus pentachloride. This product is finally condensed in accordance with known methods, for example, as described above, with 5-amino-2,4,6-triiodoisophthalic acid dichloride to obtain the finally desired tetracarboxylic acid tetrachloride of Formula II wherein $R^3$ and $R^4$ are different and signify a lower alkyl (preferably methyl) and hydrogen, respectively.

The dicarboxylic acid dichlorides of the formula Cl—CO—X—COCl or the monoester Cl—CO—X—CO.OCH$_3$ wherein X is straight-chain or branched alkylene, interrupted by one or more sulfur or selenium atoms and, optionally, additionally, interrupted by oxygen atoms, are known partially (U.S. Pat. Nos. 3,888,877, 3,966,766).

The preparation of the unknown compounds of this type can be accomplished according to conventional methods by starting with the dicarboxylic acids, known in the literature (David K. Laing et al., J.Chem.Soc. Dalton Trans. 1975 [21], 2297; J. A. Durden and H. J. Weiden, J. Agr. Food Chem. 22, 396 [1974]; U.S. Pat. Nos. 3,888,877 and 3,966,766), respectively with the monoesters HOOC—X—COOCH$_3$, obtained by esterification of the dicarboxylic acids and by partial saponification according to methods known to those skilled in the art. By reaction with thionyl chloride or oxalyl chloride, the monoester chlorides are then prepared in a manner known per se from the monoesters, or the dicarboxylic acid dichlorides are prepared from the dicarboxylic acids, as explained in detail below, using as an example the preparation of 4,4,6,6-tetramethyl-4,6-disila-5-oxa-nonanedioic acid dichloride.

The preparation of the dicarboxylic acid dichlorides of the formula ClCO—X—COCl or of the monoester chlorides of the formula ClCOX—COCH$_3$ where X is interrupted by a di(lower alkyl)silyl or a tetra(lower alkyl)disiloxane group can be accomplished by starting with the dicarboxylic acid methyl esters CH$_3$OCO—X—COOCH$_3$, which are described, for example, by R. A. Benkeser et al (J. Org. Chem. 32:395 [1967]). In this procedure, the monoesters CH$_3$OCO—X—COOH are obtained by partial saponification with only one equivalent of base according to methods known to those skilled in the art. Alternatively, the dicarboxylic acids HOOC—X—COOH are produced, likewise according to methods known to those skilled in the art, by complete saponification with an excess of the base or by interesterification in an alcoholic solution in the presence of a mineral acid. To produce the monoesters CH$_3$OCO—X—COCl from the dicarboxylic acids HOOC—X—COOH, which are described, for example, by L. H. Sommer et al (J. Amer. Chem. Soc. 75:2932 [1953]), these acids are first converted into the dicarboxylic acid diesters, from which then—as described above—the monoesters CH$_3$OCO—X—COOH are obtained by partial saponification.

By reaction with thionyl chloride or oxalyl chloride, the monoester chlorides are then prepared in a manner known per se from the monoesters, or the dicarboxylic acid dichlorides are prepared from the dicarboxylic acids, as is explained in detail below, using as an example the production of 4,4,6,6-tetramethyl-4,6-disila-5-oxanonanedioic acid dichloride.

40 ml of oxalyl chloride is added by distillation to 8.2 g of 4,4,6,6-tetramethyl-4,5-disila-5-oxanonanedioic acid, the reaction being mitigated by ice cooling. Subsequently, the reaction mixture is stirred for 45 minutes at room temperature and the excess oxalyl chloride is distilled off under vacuum. The residue is fractionated under vacuum, thus obtaining 6.2 g of 4,4,6,6-tetramethyl-4,6-disila-5-oxanonanedioic acid dichloride, b.p.$_1$ 45° C. (66% of theory).

It has been found that the compounds of Formula I of this invention are excellently suitable as opaquing materials in X-ray contrast media. Surprisingly, an aqueous solution of compounds of Formula I can also be used in direct and indirect lymphography.

Indirect lymphography is understood to mean all those methods wherein opaquing materials are introduced, for example, into the skin and subcutaneous tissue, mucosas, parenchymatous and non-parenchymatous organs, serous and cavitary sinuses, muscles and cartilage and bones.

The compounds of Formula I are very rapidly water-soluble without being burdened by the disadvantage of increased diffusion through the lymphatic vessel walls. The thus-obtained lymphograms are, therefore, distinguished by a sharp contrast with respect to the surroundings. The X-ray contrast medium preparations on the basis of the compounds of this invention are very stable, are sensitive to neither air nor light, and do not show an undesired splitting off of iodine either in pure form or in solution. As far as compatibility is concerned, the preparations have the special advantage that they do not impose a risk of embolism formation.

The storage capability of the contrast media of this invention in the lymphatic vessel system, after direct or indirect administration, is good. As early as 5-20 minutes after application, the course of the lymphatic vessels, and the lymph nodes, are optimally contrasted.

After administration, the contrast medium remains in the lymphatic system for at least 45 minutes and is excreted practically entirely via the kidney within about 24 hours. Since, in using the X-ray contrast media of this invention in lymphography, the heretofore required suitability test is unnecessary, the desired lymphogram can be produced, without in-patient treatment, whereby the treatment time is shortened to maximally 1½-4 hours.

Another very substantial advantage of the X-ray contrast media of this invention based on the compounds of Formula I is the possibility of an indirect visualization of the lymphatic system at least up to the first lymph node station, but in part also up to the second lymph node station and therebeyond. Thus, an early detection of pathological changes, for example, metastatizing, is made possible, whereby such changes can be combated in more timely fashion.

Moreover, aqueous solutions of the compounds of this invention possess a low viscosity which is at a level desirable for X-ray contrast media, making it possible to utilize smaller cannulas for these X-ray contrast media.

The following table compares the advantageous effects of the compounds of this invention in lymphography, using as test substances thiodipropionic acid bis[3,5-bis-(2,3-dihydroxypropyl-N-methylcarbamoyl)-2,4,6-triiodoanilide] (A) and 4,4,6,6-tetramethyl-4,6-disila-5-oxanonanedioic acid bis[3,5-bis(2,3-dihydroxypropyl-N-methylcarbamoyl)-2,4,6-triiodoanilide] (B) in comparison with the fatty acid ethyl ester of iodinated oleum papaveris (C). The test results were determined on dogs using testing methods conventional in lymphography after direct and indirect administration.

TABLE

| Evaluation Parameter | C | A or B |
| --- | --- | --- |
| Applicability | Direct Lymphography | Direct and Indirect Lymphography |
| Stability | Light-, Air-Sensitive | Stable |
| Compatibility | (I Cleavage) Risk of Embolism | No Embolisms |
| Residence Time in the Body | Weeks to Months | Hours |
| Visualization Range with Indirect Lymphography | No Visualization of Lymphatic System | Visualization of Lymphatic System up to at Least the First Lymph Node Station |
| Treatment period | At Least 3 Days | Maximally 4 hours |

The compounds of this invention, however, are not only suitable for lymphography. Due to their physical properties, such as, for example, high water solubility and low osmotic pressure, and their pharmacological properties, such as, for example, an extremely low diuretic effect, they are also excellently suited as opaquing materials in the various fields of application of water-soluble X-ray constant media, especially for the visualization of body cavities and also, for example, of the urine-excreting tracts, including retrograde urography, of the gastrointestinal tract, the articular cavities, the cerebrospinal and tracheobronchial systems, for hysterosalpingography, for gastroenteroscopy, for bronchoscopy, etc. In all instances, the novel X-ray contrast media provide an especially good recognizability of the details of the visualized structures.

The invention accordingly also concerns novel X-ray contrast media based on the compounds of this invention. These novel X-ray contrast media can be prepared in a manner known per se, for example, by placing the opaquing compound into a form suitable for administration along with the additives customary in galenic pharmacy, for example stabilizers, such as sodium edetate, calcium disodium edetate, physiologically compatible buffers, sodium chloride, propylene glycol, ethanol, and similar compounds. The concentration of the novel X-ray contrast media in the aqueous medium is entirely dependent on the X-ray diagnostic method. The preferred concentrations and dosages of the novel compounds, respectively range from 20 to 400 mg I/ml and from 5 to 500 ml. Concentrations of 100 to 400 mg I/ml are especially preferred.

If the compounds of this invention are to be utilized specifically for lymphography, the aqueous contrast medium solutions are prepared, for example, by stirring the corresponding active compound at room temperature into water for injection purposes, until the substance is completely dissolved. By adding alcohols, bases, acids or the usual buffer systems, the properties of the solution can be tailored as desired. For this field of application, the preferred concentrations and dosages are in the ranges of 200 to 400 mg I/ml and 1 to 50 ml, respectively.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Thiodipropionic Acid
Bis[3,5-bis(2,3-dihydroxypropyl-N-methylcarbamoyl)-2,4,6-triiodoanilide]

(A) Thiodipropionic Acid
Bis(3,5-chlorocarbonyl)-2,4,6-triiodoanilide 595.7 g of 5-amino-2,4,6-triiodoisophthalic acid dichloride is dissolved in the hot state in 600 ml of dioxane. Under agitation, 97.3 ml of thiodipropionic acid dichloride is added dropwise within 20 minutes to the boiling solution. The reaction mixture is then stirred under reflux (bath temperature 120–130°) for 4 hours. After about 1 hour, a precipitate is produced. After agitation overnight at room temperature the precipitate is vacuum-filtered and dried at 50° under vacuum over caustic soda without air flow. Crude yield: 543 g (81.4% of theory). The crude "tetrachloride" is again extracted for 30 minutes with 750 ml of dioxane on a steam bath, vacuum-filtered after cooling to room temperature, washed with a small amount of dioxane, and dried without air flow at 50° under vacuum over caustic soda. Yield: 435 g (61% of theory) with 6.5% dioxane, m.p. 253°–254° (decomposition).

(B) Amidation 285 g of thiodipropionic acid bis(3,5-chlorocarbonyl)-2,4,6-triiodoanilide is dissolved in 500 ml of dimethylacetamide and heated to 50°. At 50°, 105 g of N-methylamino-2,3-propanediol, dissolved in 300 ml of dimethylacetamide, is added dropwise within 45 minutes under agitation, the mixture heating up to +58°. 237.6 ml of tributylamine is added to the reaction mixture, then the latter is stirred for 4 hours at about 50° and overnight at room temperature. The reaction mixture is thereafter combined with 40 ml of concentrated hydrochloric acid until an acidic reaction is obtained and stirred dropwise into 4 l of methylene chloride. After 30 minutes of agitation the precipitate is vacuum-filtered, again extracted for 30 minutes with 1.5 l of methylene chloride, vacuum-filtered, and dried under vacuum at 40°.

Crude yield: 364 g.

200 g of crude product (pH 4–5) is dissolved under heating in 2 l of methanol and passed, after filtering, over a weakly alkaline anion exchanger, for example "Lewatit" MP 7080, about 5 l. Dropping speed about 1 liter/hour. The solution is discharged with a pH of about 10. The filtrate is concentrated to 2 l on a "Rotavapor" rotary evaporator. The thus-obtained methanolic solution is then passed over a weakly acidic cation exchanger, for example "Lewatit" CP 3050, 5 l. The solution is discharged colorless and with a pH of >6. The thus-obtained methanolic solution is concentrated to 1.2 l. Under boiling heat, 2.4 l of isopropanol is then added dropwise. An oily deposit is thus formed which solidifies upon cooling. After agitation overnight, the precipitate is vacuum-filtered, washed in the cold state with a small amount of isopropanol, and extracted with ethanol. The solid residue is vacuum-filtered. After drying under vacuum at 100°, 100 g of thiodipropionic acid bis[3,5-bis(2,3-dihydroxypropyl-N-methylcarbamoyl)-2,4,6-triiodoanilide] is obtained, m.p. 240°–260° (decomposition).

EXAMPLE 2

20 g of thiodipropionic acid bis[3,5-bis(chlorocarbonyl)-2,4,6-triiodoanilide] is dissolved in 50 ml of dimethylacetamide and heated to 50°. At 50°, 6.8 g of 1-amino-2,3-propanediol is added dropwise within 30 minutes under agitation, this step being slightly exothermic. 17.8 ml of tributylamine is added to the mixture, and the latter is stirred for 4 hours at 50° and overnight at room temperature. The reaction mixture is then acidified with concentrated hydrochloric acid and stirred dropwise into 300 ml of methylene chloride. After vacuum-filtering and washing of the precipitate with methylene chloride, the product is dried under vacuum at 40°. The crude product is passed over a weakly alkaline anion exchanger prepared in dimethylacetamide and then over a weakly acidic cation exchanger, thus obtaining an almost colorless solution which is concentrated to 200 ml. At this point in time, about 800 ml of isopropanol is added. The evolving precipitate is vacuum-filtered, washed with isopropanol, and extracted with a small amount of water. The precipitate is dried for 10 hours at 50° under vacuum, thus obtaining 17.5 g (75% of theory) of thiodipropionic acid bis[3,5-bis(2,3-dihydroxypropylcarbamoyl)-2,4,6-triiodoanilide], m.p. 300° (decomposition).

EXAMPLE 3

20 g of thiodipropionic acid bis[3,5-bis(chlorocarbonyl)-2,4,6-triiodoanilide] is gradually introduced into a mixture of 200 ml of dioxane and 42 g of N-methyl-1,3-propanediol, heated to 50°. The solid tetrachloride is rapidly dissolved under heating. The mixture is stirred for 2 hours at 50°. After cooling, 200 ml of dichloromethane is stirred into the suspension. The mixture is decanted off from the oily deposit and taken up in 50 ml of methanol. The methanolic solution is allowed to flow into 500 ml of isopropanol, and the precipitate is vacuum-filtered. For further purification the crude product is dissolved in a mixture of methanol/dimethylacetamide and purified as described in Example 1. Yield: 19.2 g (82% of theory) of thiodipropionic acid bis[3,5-bis(1,3-dihydroxypropyl-N-methylcarbamoyl)-2,4,6-triiodoanilide], m.p. 300° (decomposition).

EXAMPLE 4

59.5 g of 5-amino-2,4,6-triiodoisophthalic acid dichloride is condensed with 12 g of dithiodiacetic acid dichloride as described in Example 1(A). Yield: 34.8 g (52% of theory) of dithiodiacetic acid bis[3,5-bis(chlorocarbonyl)-2,4,6-triiodoanilide], m.p. 285° (decomposition). 20 g of this tetrachloride is reacted with 7.9 g of N-methylamino-2,3-propanediol, as described in Example 1(B). After the reaction mixture has been worked up by precipitation into methylene chloride, removal of the anions and cations by means of weakly alkaline and weakly acidic ion exchangers, and reprecipitation from methanol/isopropanol 1:2), 12 g (60% of theory) of dithiodiacetic acid bis[3,5-bis(2,3-dihydroxypropyl-N-methylcarbamoyl)-2,4,6-triiodoanilide] is obtained, m.p. 235° (decomposition).

EXAMPLE 5

As described in Example 1(A), 59.5 g of 5-amino-2,4,6-triiodoisophthalic acid dichloride is condensed with 13.5 g of bis(2-chlorocarbonylethyl)disulfide. Yield: 42.2 g (62% of theory) of 4,5-dithiaoctanedioic acid bis[3,5-bis(chlorocarbonyl)-2,4,6-triiodoanilide], m.p. 252°. As described in Example 1(B), 40 g of this tetrachloride is reacted with 15.2 g of N-methylamino- 2,3-propanediol. After the mixture has been worked up by precipitation into methylene chloride, removal of the anions and cations by means of weakly alkaline and weakly acidic ion exchangers, and reprecipitation from methanol/isopropanol (1:2), 30 g (63% of theory) of 4,5-dithiaoctanedioic acid bis[3,5-bis(2,3-dihydroxypropyl-N-methylcarbamoyl)-2,4,6-triiodoanilide] is obtained, m.p. 290°–292.5° (decomposition).

EXAMPLE 6

59.5 g of 5-amino-2,4,6-triiodoisophthalic acid dichloride is condensed with 11 g of 2-methyl-3-thiaglutaric acid dichloride as described in Example 1(A), thus obtaining a mixture of 5,5′-(2-methyl-3-thiaglutaryldiimino)-bis(2,4,6-triiodoisophthalic acid dichloride) and 5-(2-methyl-3,5-dioxoperhydro-1,4-thiazin-4-yl)-2,4,6-triiodoisophthalic acid dichloride; this mixture is separated by chromatography on silica gel. With chloroform as the eluent, the first product separated is 5-(2-methyl-3,5-dioxoperhydro-1,4-thiazin-4-yl)-2,4,6-triiodoisophthalic acid dichloride and then 5,5′-(2-methyl-3-thiaglutaryldiimino)-bis(2,4,6-triiodoisophthalic acid dichloride is obtained as a pure compound. The yield is 15.5 g (24% of theory), m.p. 255° (decomposition). 10 g of this tetrachloride is reacted as described in Example 1(B) with 4 g of N-methylamino-2,3-propanediol. After the mixture has been worked up by precipitation into methylene chloride, removal of the anions and cations by means of weakly alkaline and weakly acidic ion exchangers, and reprecipitation from methanol/isopropanol (1:2), the yield is 6 g (50% of theory) of 5,5′-(2-methyl-3-thiaglutaryldiimino)-bis[2,4,6-triiodoisophthalic acid (2,3-dihydroxypropyl-N-methyl)diamide], m.p. 235°–320° (decomposition).

EXAMPLE 7

59.5 g of 5-amino-2,4,6-triiodoisophthalic acid dichloride is condensed as described in Example 1(A) with 13.5 g of 3,6-dithiaoctanedioic acid dichloride, thus obtaining 36.8 g (54% of theory) of 3,6-dithiaoctanedioic acid bis[3,5-bis(chlorocarbonyl)-2,4,6-triiodoanilide], m.p. 270° (decomposition). 30 g of this tetrachloride is reacted with 11.5 g of N-methyl-amino-2,3-propanediol as described in Example 1(B). After the mixture has been worked up by precipitation into methylene chloride, removal of the anions and cations by means of weakly alkaline and weakly acidic ion exchangers, and reprecipitation from methanol/isopropanol (1:2), 20 g (55% of theory) of 3,6-dithiaoctanedioic acid bis[3,5-bis(2,3-dihydroxypropyl-N-methylcarbamoyl)-2,4,6-triiodoanilide] is obtained, m.p. 245° (decomposition).

EXAMPLE 8

59.5 g of 5-amino-2,4,6-triiodoisophthalic acid dichloride is condensed with 15.1 g of 3,8-dithiadecanedioic acid dichloride as set forth in Example 1(A). Yield: 40.5 g (58% of theory) of 3,8-dithiadecanedioic acid bis[3,5-bis(chlorocarbonyl)-2,4,6-triiodoanilide], m.p. 245°. 30 g of this tetrachloride is reacted with 11.5 g of N-methylamino-2,3-propanediol as described in Example 1(B). After the mixture has been worked up by precipitation into methylene chloride, removal of the anions and cations by means of weakly alkaline and weakly acidic ion exchangers, and reprecipitation from methanol/isopropanol (1:2), 22 g (59% of theory) of 3,8-dithiadecanedioic acid bis[3,5-bis(2,3-dihydroxypropyl-N-methylcarbamoyl)-2,4,6-triiodoanilide] is obtained, m.p. 250° (decomposition).

EXAMPLE 9

59.5 g of 5-amino-2,4,6-triiodoisophthalic acid dichloride is condensed, as indicated in Example 1(A), with 14.4 of 4-selenaheptanedioic acid dichloride. Yield: 37.5 g (54% of theory) of 4-selenaheptanedioic acid bis[3,5-bis(chlorocarbonyl)-2,4,6-triiodoanilide], m.p. 246° (decomposition). 30 g of this tetrachloride is reacted, as set forth in Example 1(B), with 11.4 g of N-methylamino-2,3-propanediol. After the mixture has been worked up by precipitation into methylene chloride, removal of the anions and cations by means of weakly alkaline and weakly acidic ion exchangers, and reprecipitation from methanol/isopropanol (1:2), the yield is 16.4 g (46% of theory) of 4-selenaheptanedioic acid bis[3,5-bis(2,3-dihydroxypropyl-N-methylcarbamoyl)-2,4,6-triiodoanilide], m.p. 215°–260° (decomposition).

EXAMPLE 10

As described in Example 1(A), 59.5 g of 5-amino-2,4,6-triiodoisophthalic acid dichloride is condensed with 12.9 g of 3,5-dithiaheptanedioic acid dichloride, thus obtaining 41.3 g (61% of theory) of 3,5-dithiaheptanedioic acid bis[3,5-bis(chlorocarbonyl)-2,4,6-triiodoanilide], m.p. 240/250° (decomposition). 30 g of this tetrachloride is reacted as described in Example 1(B) with 11.7 g of N-methylamino-2,3-propanediol. After the mixture has been worked up by precipitation into dichloromethane, the crude product is taken up in water and extracted with carbon. The raw solution is filtered over an adsorber resin; the discharged, aqueous solution is tested for its ion content by means of measuring the conductivity. The substance adsorbed on the resin is eluted with ethanol after exhaustive washing with water. The thus-prepurified substance is filtered for purifying purposes over a weakly alkaline and a weakly acidic exchanger. After reprecipitation of the thus-isolated crude product from methanol/isopropanol (1:2), 24.4 g (69% of theory) of 3,5-dithiaheptanedioic acid bis[3,5-bis(2,3-dihydroxypropyl-N-methylcarbamoyl)-2,4,6-triiodoanilide] is obtained, m.p. 290° decomposition.

EXAMPLE 11

59.5 g of 5-amino-2,4,6-triiodoisophthalic acid dichloride is condensed with 14.4 g of 4,6-dithianonanedioic acid dichloride as described in Example 1(A). Yield: 37.1 g (53.7% of theory) of 4,6-dithianonanedioic acid bis[3,5-bis-(chlorocarbonyl)-2,4,6-triiodoanilide], m.p. 220°–260° (decomposition). 25 g of this tetrachloride is reacted, as set forth in Example 1(B), with 10 g of N-methylamino-2,3-propanediol. After the mixture has been worked up by precipitation into methylene chloride, removal of the anions and cations by means of weakly alkaline and weakly acidic ion exchangers, and reprecipitation of the thus-obtained crude product from methanol/isopropanol (1:2), 17.3 g (55% of theory) of 4,6-dithianonanedioic acid bis[3,5-bis(2,3-dihydroxypropyl-N-methylcarbamoyl)-2,4,6-triiodoanilide] is obtained, m.p. 230°–260° (decomposition).

EXAMPLE 12

4-Thiapentanedioic Acid Mono-[3,5-bis(2,3-dihydroxypropyl-N-methylcarbamoyl)-2,4,6-triiodoanilide]-mono-[3,5-bis(2,3-dihydroxypropyl-N-methylcarbamoyl)2,4,6-triiodo-N-methylanilide]

(A) 115 g of 5-methylamino-2,4,6-triiodoisophthalic acid dichloride is dissolved at room temperature in 80 ml of dimethylacetamide. 44.6 g of thiodipropionic acid monomethylate monochloride is added dropwise to the reaction mixture, the temperature being maintained at below 30°. After 24 hours of agitation, the thus-precipitated by-product is vacuum-filtered and the filtrate concentrated under vacuum. The oily residue is chromatographed with methylene chloride over silica gel. The fractions containing the pure compound are combined, the solution is concentrated, and the residue is extracted with 100 ml of dry ether, thus obtaining 71 g (47% of theory) of 2,4,6-triiodo-3-[N-methyl-N-(methoxy-4-thiapimeloyl)amino]isophthalic acid dichloride, m.p. 153°. 31.2 g of this monoester is suspended in 300 ml of a dioxane/water mixture (1:1) and combined at 80° with 1 equivalent (120 millimoles) of sodium hydroxide solution. After 4 hours the mixture is allowed to cool, agitated overnight, and concentrated under vacuum. The residue is taken up in a small amount of methanol and stirred into prepared acetone. The thus-obtained precipitate is vacuum-filtered and dried for 3 hours under vacuum at 50°, thus obtaining 17.2 g (54% of theory) of 2,4,6-triiodo-3-]N-methyl-N-(hydroxy-4-thiapimeloyl)amino]isophthalic acid as the trisodium salt, m.p. 300° (decomposition). 15 g of this trioic acid is suspended in 150 ml of toluene, and any water present is removed by azeotropic distillation. At 10°, 17.9 g of phosphorus pentachloride is introduced and the mixture is stirred for 2 hours. The reaction solution is then concentrated under vacuum at about 10°; yield: 17.5 g (108% of theory) of crude 2,4,6-triiodo-3-[N-methyl-N-(chloro-4-thiapimeloyl)amino]isophthalic acid dichloride.

17 g of this crude, moisture-sensitive trioic acid chloride is introduced under nitrogen in incremental portions into a solution of 12.8 of 5-amino-2,4,6-triiodoisophthalic acid dichloride in 25 ml of dimethylacetamide. The mixture is stirred for 16 hours at 30° and the thus-precipitated tetrachloride is vacuum-filtered. The crude product is dissolved in 150 ml of trichloromethane and filtered over silica gel, thus obtaining 15.3 g of 4-thiaheptanedioic acid mono-[3,5-bis(chlorocarbonyl)-2,4,6-triiodo-N-methylanilide]-mono-[3,5-bis(-chlorocarbonyl)-2,4,6-triiodoanilide] ("tetrachloride"), m.p. 240°-260° (decomposition).

(B) Amidation 15 g of the tetrachloride is introduced into 21 g of N-methyl-2,3-propanediol heated to 50°-60° and under a nitrogen atmosphere. The reaction mixture is allowed to stand for 4 hours at this temperature and then combined with 25 ml of dry dioxane. The dioxane is decanted, the residue is taken up in 50 ml of methanol, and the mixture is precipitated with 250 ml of isopropanol. The precipitated crude product is vacuum-filtered and freed of ions analogously to Example 1. Yield: 11.2 g of 4-thiapentanedioic acid mono-[3,5-bis(2,3-dihydroxypropyl-N-methylcarbamoyl)-2,4,6-triiodoanilide]-mono-[3,5-bis(2,3-dihydroxypropyl-N-methylcarbamoyl)2,4,6-triiodo-N-methylanilide], m.p. 250°(decomposition).

EXAMPLE 13

20 g of thiodipropionic acid bis[3,5-bis(chlorocarbonyl)-2,46-triiodoanilide] is dissolved in 50 ml of dimethylformamide and, at room temperature, 29.2 g of methylglucamine, suspended in 50 ml of dimethylformamide, is added dropwise to the reaction mixture. The mixture heats up during this step. After 4 hours of agitation at 50° the mixture is cooled and stirred into 500 ml of isopropanol. The precipitate is vacuum-filtered, taken up in methanol/dimethylformamide, and purified as described in connection with Example 1, thus obtaining 21 g (70% of theory) of thiodipropionic acid bis[3,5-bis(2,3,4,5,6-pentahydroxyhexyl-N-methylcarbamoyl)-2,4,6-triiodoanilide], m.p. 230° (decomposition).

EXAMPLE 14

59.5 g of 5-amino-2,4,6-triiodoisophthalic acid dichloride is condensed with 12.7 g of 3-oxa-6-thiaoctanedioic acid dichloride as described in Example 1(A), thus obtaining 34 g (50.6% of theory) of 3-oxa-6-thiaoctanedioic acid bis[3,5-bis(chlorocarbonyl)-2,4,6-triiodoanilide], m.p. 272°-290° (decomposition). 23.7 g of this tetrachloride is reacted with 7.8 g of N-methylamino-2,3-propanediol as set forth in Example 1(B). The reaction solution is stirred into 1 liter of isopropanol. The thus-precipitated compound is vacuum-filtered, washed with isopropanol, and dried. The crude compound is dissolved in methanol and purified as described in connection with Example 1 by filtration over ion exchangers and reprecipitation from methanol/isopropanol (1:2). Yield: 11.7 g (49% of theory) of 3-oxa-6-thiaoctanedioic acid bis[3,5-bis(2,3-dihydroxypropyl-N-methylcarbamoyl)2,4,6-triiodoanilide], m.p. 285°-290° (decomposition).

EXAMPLE 15

4,4,6,6-Tetramethyl-4,6-disila-5-oxanonanedioic Acid Bis[3,5bis(2,3-dihydroxypropyl-N-methylcarbamoyl)-2,4,6-triiodoanilide]

(A) 4,4,6,6-Tetramethyl-4,6-disila-5-oxanonanedioic Acid Bis[3,5bis(chlorocarbonyl)-2,4,6-triiodoanilide] ("Tetrachloride")

19.4 g of 5-amino-2,4,6-triiodoisophthalic acid dichloride is dissolved under heating in 20 ml of dioxane; within 10 minutes, 6.2 g of 4,4,6,6-tetramethyl-4,6-disila-5-oxanonanedioic acid dichloride is added dropwise under boiling to the reaction solution. The mixture is refluxed for 4 hours and then allowed to stand overnight at room temperature. The mixture is then vacuum-filtered, the filtration residue is washed with a small amount of cold dioxane, and recrystallized from benzene, thus obtaining 9.25 g of "tetrachloride"=4,4,6,6-tetramethyl-4,6-disila-5-oxanonanedioic acid bis[3,5bis(-chlorocarbonyl)-2,4,6-triiodoanilide], m.p. 212°-213° (40% of theory).

(B) At 40°, 7 g of "tetrachloride" is added dropwise to a solution of 6.14 g of N-methylamino-2,3-propanediol in 25 ml of dimethylacetamide (DMA). The solution is then maintained for 2 hours at 50° and stirred into 250 ml of isopropyl ether. The oil precipitate is dissolved in a small amount of methanol, again precipitated into isopropyl ether to remove residue DMA, and the precipitate is filtered off. For further purification, the residue is dissolved in 350 ml of methanol and the solution is filtered first over a weakly alkaline anion exchanger ("Lewatit" MP 7080) and then over a weakly acidic cation exchanger ("Lewatit" CP 3050). After evaporation, 7.8 g of 4,4,6,6-tetramethyl-4,6-disila-5-oxanonanedioic acid bis[3,5-bis(2,3-dihydroxypropyl-N-methylcarbamoyl)-2,4,6-triiodoanilide] is obtained (93% of theory), decomposition poit 220°.

EXAMPLE 16

5,5-Dimethyl-5-silanonanedioic Acid Bis[3,5-bis(2,3-dihydroxypropyl-N-methylcarbamoyl)-2,4,6-triiodoanilide]

(A) 5,5-Dimethyl-5-silanonanedioic Acid Bis[3,5-bis(chlorocarbonyl)-2,4,6-triiodoanilide] ("Tetrachloride")

8.4 g of 5-amino-2,4,6-triiodoisophthalic acid dichloride is dissolved by heating in 9 ml of dioxane, and 4.5 g of 5,5-dimethyl-5-silanonanedioic acid dichloride is added dropwise within 10 minutes under boiling. The mixture is refluxed for 3.5 hours and allowed to stand overnight at room temperature. The mixture is then vacuum-filtered, the filtration residue is washed with a small amount of cold dioxane, and the test compound is recrystallized from benzene, thus obtaining 4.76 g of "tetrachloride" (49% of theory), m.p. 225°-230° (decomposition).

(B) From 4.75 g of "tetrachloride" and 4.3 g of N-methylamino-2,3-propanediol, 5.1 g of 5,5-dimethyl-5-silanonanedioic acid bis[3,5-bis(2,3dihydroxypropyl-N-methylcarbamoyl)-2,4,6-triiodoanilide] is obtained as described in Example 1(B) (90% of theory), decomposition point 225°.

EXAMPLE 17

4,4-Dimethyl-4-silaheptanedioic Acid Bis[3,5-bis(1,3-dihydroxypropylcarbamoyl)-2,4,6-triiodoanilide]

(A) 4,4-Dimethyl-4-silaheptanedioic Acid Bis[3,5-bis(chlorocarbamoyl)-2,4,6-triiodoanilide] ("Tetrachloride")

6.3 g of 5-amino-2,4,6-triiodoisophthalic acid dichloride and 1.5 g of 4,4-dimethyl-4-silaheptanedioic acid dichloride are reacted, as described in Example 1(A), to obtain 2.9 g of "tetrachloride" (40% of theory); decomposition point about 215°.

(B) The thus-obtained "tetrachloride" (2.9 g) is reacted as described in Example 1(B) with 2.3 g of 2-amino-1,3-propanediol to produce 2.69 g of 4,4-dimethyl-4-silaheptanedioic acid bis[3,5-bis(1,3-dihydroxypropylcarbamoyl)-2,4,6-triiodoanilide] (80% of theory), decomposition point 230°.

EXAMPLE 18

Preparation of a Ready-For-Use X-Ray Contrast Medium Solution for Lymphography

A solution of 61.68 g of 4,4,6,6-tetramethyl-4,6-disila-5-oxanonanedioic acid bis[3,5-bis(2,3-dihydroxypropyl-N-methylcarbamoyl)-2,4,6-triiodoanilide], 10 mg of anhydrous calcium disodium edetate, and 4.0 g of 1,2-propanediol in 90 ml of bisdistilled water is adjusted to pH 7.2 by adding 0.1 N sodium hydroxide solution and then filled up to 100 ml with bidistilled water. This solution is dispensed into ampoules or "Multivials" and sterilized for 20 minutes at 120°. This solution contains 275 mg of iodine per milliliter.

EXAMPLE 19

Preparation of a Ready-For-Use X-Ray Contrast Medium Solution for Lymphography 58.09 g of 3,3'-thiodipropionic acid bis[3,5-bis(2,3-dihydroxypropyl-N-methylcarbamoyl)-2,4,6-triiodoanilide], 10 mg of anhydrous calcium disodium edetate, and 4.0 g of 1,2-propanediol are dissolved in 90 ml of bidistilled water; the pH of this solution is set to 7.2 by adding 0.1 N sodium hydroxide solution, and finally the volume is filled up to 100 ml with bidistilled water. The solution is passed through a porous filter having a porosity of 0.2 μm, filled into ampoules or "Multivials" and sterilized for 20 minutes at 120°. The solution contains 275 mg of iodine per milliliter.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

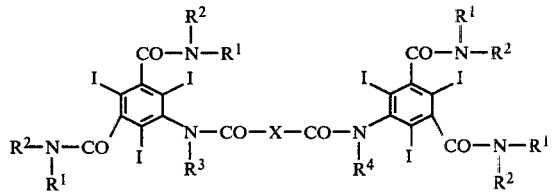

wherein $R^1$ is hydroxy-$C_{2-8}$-alkyl containing 1–5 OH groups;

$R^2$ is hydrogen, $C_{1-4}$-alkyl, or $R^1$;

$R^3$ and $R^4$ can be identical or different, and each independently is hydrogen or $C_{1-4}$-alkyl; and X is straight chain or branched $C_{2-12}$ alkylene interrupted by 1–4 sulfur or selenium atoms, and, optionally, additionally interrupted by 1–3 oxygen atoms, by a di($C_{1-4}$-alkyl)silyl group or a tetra ($C_{1-4}$-alkyl)disiloxane group.

2. A compound of claim 1, wherein $R^1$ is a $C_{2-4}$-straight chain alkyl substituted by 1–3 OH groups.

3. A compound of claim 1, wherein $R^1$ is a branched $C_{3-5}$-alkyl substituted by 1–3 OH groups.

4. A compound of claim 2 or 3 wherein $R^1$ contains two OH groups.

5. A compound of claim 1, wherein $R^2$, $R^3$ and $R^4$ are straight chain $C_{1-2}$-alkyl.

6. A compound of claim 1, wherein X is straight chain $C_{2-4}$-alkylene interrupted by 1–3 S atoms or 1–2 Se atoms.

7. A compound of claim 1, wherein X is $C_{2-8}$-alkylene interrupted by a di($C_{1-4}$ alkyl)silyl group or a tetra($C_{2-8}$ alkyl)disiloxane group.

8. 3,3'-Thiodipropionic acid bis[3,5-bis(2,3-dihydroxypropyl-N-methylcarbamoyl)-2,4,6-triiodoanilide], a compound of claim 1.

9. 3,6-Dithiaoctanedioic acid bis(3,5-bis(2,3-dihydroxypropyl-N-methylcarbamoyl)-2,4,6-triiodoanilide], a compound of claim 1.

10. 4,4,6,6-Tetramethyl-4,6-disila-5-oxanonanedioic acid bis[3,5-bis(2,3-dihydroxypropyl-N-methylcarbamoyl)-2,4,6-triiodoanilide], a compound of claim 1.

11. A pharmaceutical X-ray contrast medium comprising an amount of a compound of claim 1 or 8 effective as an X-ray opaque agent, and a pharmaceutically acceptable carrier.

12. The pharmaceutical X-ray contrast medium of claim 11 comprising 20–400 mg I/ml of total composition of the opaque agent.

13. A method of X-ray visualization of a body part of a host which comprises prior to the taking of X-rays, administering to the host an amount of a compound of claim 1 or 8 effective as an X-ray opaque agent for the body part to be visualized and, subsequently, taking X-rays of the body part to be visualized.

14. The method of claim 13, wherein the visualization is by lymphography.

15. A method of rendering a body part of a host visualizable by X-rays, which comprises administering to the host an amount of a compound of claim 1 or 8 effective as an X-ray opaque agent for the body part to be visualized.

* * * * *